US010340032B2

(12) United States Patent
Ramsey et al.

(10) Patent No.: US 10,340,032 B2
(45) Date of Patent: Jul. 2, 2019

(54) RAPIDLY CONFIGURABLE DRUG DETECTION SYSTEM WITH ENHANCED CONFIDENTIALITY

(71) Applicants: James Taylor Ramsey, Portsmouth, VA (US); Stephen David Gobin, Portsmouth, VA (US)

(72) Inventors: James Taylor Ramsey, Portsmouth, VA (US); Stephen David Gobin, Portsmouth, VA (US)

( * ) Notice: Subject to any disclaimer, the term of this patent is extended or adjusted under 35 U.S.C. 154(b) by 88 days.

(21) Appl. No.: 16/038,512

(22) Filed: Jul. 18, 2018

(65) Prior Publication Data

US 2019/0057759 A1 Feb. 21, 2019

Related U.S. Application Data

(60) Provisional application No. 62/546,135, filed on Aug. 16, 2017.

(51) Int. Cl.
*G16H 10/40* (2018.01)
*G01N 33/94* (2006.01)
*G16H 10/60* (2018.01)
*G16H 80/00* (2018.01)

(52) U.S. Cl.
CPC .......... *G16H 10/40* (2018.01); *G01N 33/946* (2013.01); *G01N 33/9486* (2013.01); *G16H 10/60* (2018.01); *G16H 80/00* (2018.01)

(58) Field of Classification Search
CPC ........ G16H 10/40; G16H 10/60; G16H 80/00; G01N 33/9486; G01N 33/946
See application file for complete search history.

(56) References Cited

U.S. PATENT DOCUMENTS 8,344,836 B2 1/2013 Lauder et al.
2018/0164295 A1* 6/2018 Karlovac ............. G01N 33/525

OTHER PUBLICATIONS

"Smart Screens Privacy Policy" Jul. 12, 2017, https://smartscreens.net/pages/smart-oral-kits. (Year: 2017).*
Carrio et al, "Automated Low-Cost Smartphone-Based Lateral Flow SalivaTest Reader for Drugs-of-Abuse Detection" Sensors 2015, 15, 29569-29593 (Year: 2015).*

(Continued)

*Primary Examiner* — Dennis White
(74) *Attorney, Agent, or Firm* — Stephen E. Zweig

(57) ABSTRACT

Point of care drug of abuse test system configured to allow a small number of general test kits to be used to analyze many different combinations of analytes, while preserving privacy and the chain of custody. The system uses disposable multiple-analyte test kits and allows the operator to select which subset of kit analytes to run. The computerized device images the test kits and transmits test results to a remote server along with a test specific ID code. The test kit is often obfuscated so that the local operator cannot interpret the results. Other donor information, such as driver's licenses and signatures, are also obtained and transmitted as well. The remote server uses the test specific ID code to retrieve an obfuscation code (answer key) from the server's database, allowing the server to interpret the results. The annotated results are transmitted to a recipient along with suitable donor verification information.

18 Claims, 11 Drawing Sheets

(56) References Cited

OTHER PUBLICATIONS

"Smart Screens™, the next generation drug testing system", uploaded to https://vimeo.com/232157802 by inventors James Taylor Ramsey and Stephen David Gobin DBA "Smart Screens" on Sep. 2, 2017.

"Welcome to Smart Screens on Vimeo", uploaded to https://vimeo.com/255424927 by inventors James Taylor Ramsey and Stephen David Gobin DBA "Smart Screens" on Feb. 12, 2018.

"How Smart Screens works", uploaded to https://vimeo.com/255425195 by inventors James Taylor Ramsey and Stephen David Gobin DBA "Smart Screens" on Feb. 12, 2018.

"Smart Screens—the future of drug testing", uploaded to https://vimeo.com/277788869 by inventors James Taylor Ramsey and Stephen David Gobin DBA "Smart Screens" on Jun. 30, 2018.

\* cited by examiner

Fig. 10B

| | | |
|---|---|---|
| FEN | Fentynl | 50 ng/mL | Negative |
| K2 | Spice | 10 ng/mL | Negative |
| THC | Marijuana | 50 ng/mL | Negative |
| MTD | Methadone | 300 ng/mL | Negative |
| mAMP | mAmphetamine | 500 ng/mL | Negative |
| OPI | Opiates | 300 ng/mL | Negative |
| OXY | Oxycodone | 100 ng/mL | Negative |
| PPX | Propoxy | 300 ng/mL | Negative |
| TRM | Tramadol | 200 ng/mL | Negative |
| PCP | Phencyclidine | 25 ng/mL | Negative |

This drug screen has produced a negative result for the drugs and cutoff levels shown beside each assay result.

No further testing is required.

NEGATIVE

COLLECTION DETAILS

Temperature in range
Volume in range
Lot # 22309A
Exp. date 12222021
DID 0098f7dh363
Collected 09222017 - 12:43pm
Reported 09222017 - 12:55pm

DONOR SIGNATURE

RAPIDLY CONFIGURABLE DRUG DETECTION SYSTEM WITH ENHANCED CONFIDENTIALITY

BACKGROUND OF THE INVENTION

Field of the Invention

This invention is in the field of rapid diagnostics tests systems for drugs of abuse.

Description of the Related Art

According to prior art, samples suspected of containing drugs of abuse are typically tested in either dedicated laboratories, or by use of on-site test kits.

Such on-site test kits often are based on multiple-track lateral flow immunoassay technology. In one type of kit, for example, antibodies specific to various types of drugs may be immobilized at different locations on the surface of different bibulous membrane tracks. A test sample suspected of containing one or more drugs is applied to the bottom of the various tracks, a carrier fluid is applied along and one or more detection labels. If no corresponding drug is present, then the detection label can bind to the corresponding antibody, often producing an optically detectable signal such as a visible line. However, if a corresponding drug is present, it can prevent the detection label from binding to the corresponding antibody, producing another optically detectable signal, such as the absence of a visible line. Suitable controls are also usually provided to detect common test errors.

Although at least some of such tests can be read directly by the human eye, often various types of computerized optical readers are used for such purposes.

Thus, according to prior art, the drug testing industry, and point of care diagnostic centers, provide test strips and test kits with test and control lines. Each strip can hold at least one or more assays or tests. Test kits are capable of detecting 1, 6, 10, 12, 18, 23 different analytes (e.g. drugs of abuse) and the like have been devised. Such test kits often have a limited shelf life, such as 18-24 months, after which they must be discarded if not used.

Although the results of drugs of abuse testing can be important for many different situations, various medical privacy acts, such as the substance abuse confidentiality regulations (SAMHSA), Health Insurance Portability and Accountability act of 1996 (HIPAA), and other regulations must be respected. In particular, such records often need to be handled with at least some degree of confidentiality.

BRIEF SUMMARY OF THE INVENTION

The invention is based, in part, on the insight that for various reasons, operators and other users of various types of diagnostics, in particular drugs of abuse type diagnostics, often have different panels of analytes that they wish to analyze. For example, an operator in one state may wish to test for the presence or absence of THC (active ingredient of marijuana), while an operator in a different state may not wish to test this. An athletics institution may be more interested in only screening for performance-enhancing drugs. Regulatory requirements also differ according to a patchwork of different Federal laws, State laws, Local laws, occupation-specific regulations, and the like. Thus, for various reasons, some historical, and some regulatory, different institutions and corporations often require screening for different types of drugs and different combinations of drugs.

Due to the previously discussed medical privacy considerations and other legal considerations, it is often undesirable for a drug screening operator to at least not receive information pertaining to the status of those drugs that have not been specifically authorized to be tested.

The invention is also based, in part, on the insight that from the logistical and cost standpoint, it is easier to provide a smaller variety of higher-volume standardized diagnostic test kits (such as dry reagent test kits configured with multiple lateral-flow immunoassays), then it is to provide large variety of different, low volume test kits, each customized to requirements of a small number of different institutions.

The invention is also based, in part, on the insight that although an operator required to only run six analytes could, in principle, run these analytes on a test kit configured to simultaneously run twelve analytes, this causes privacy problems. In addition to the fact that an operator may object to paying for more tests than needed, an additional problem is caused by lack of privacy.

Specifically, the operator will be receiving information on the presence or absence of six additional drugs that the sample donor may not have consented to, and that are not required for this particular screen.

This privacy problem is particularly acute for optically read lateral-flow immunoassays. The results of such immunoassays can be seen, often directly by the human eye, by the presence or absence of a visible "line". If the operator knows which tracks and which lines correspond to which assays, then privacy problems can occur. For example, an operator, seeing a potential "positive" on a THC line, would know that the sample donor was likely positive for THC, even though the donor would not have consented to this test, and even though that might not be an issue for that particular state or institution.

The invention is also based, in part, on the insight that some of logistical and cost problems can be at least partially resolved by providing a smaller variety of test kits configured to run a large number of different types of analytes, thus reducing costs through higher manufacturing volumes, thus making it economically feasible to not use every test result produced by the test kit. At the same time, the invention is also based, in part, on the insight that the privacy problems can be resolved if the test operator does not receive the results for tests that were not requested and donor consented to. In this case, this would resolve the previously discussed medical privacy issues and other legal considerations.

The present invention thus provides a system and method designed to help achieve the above logistical, cost, and privacy objectives. Specifically, the present invention provides diagnostic test kit and reader system that provides a standardized diagnostic test kit (often a dry-reagent test kit, such as a test kit comprising multiple lateral flow immunoassay channels) that allows the operator to select some or all of the various assays, and but then only reports those results that have been selected.

Thus, in some embodiments, the invention is a multiple-analyte diagnostic test kit, computerized optical test-kit reader and optional server system that allows the operator to select any combination of tests to be performed that is supported by the multiple-analyte test kit. However, in at least some embodiments, the invention is also designed to preserve the sample donor's privacy so that only those results that were specifically selected by the operator are reported.

Thus, in some embodiments, the invention may be a sample analysis system comprising a computerized device, such as a handheld tablet computerized device comprising a processor, camera, device software, memory, user interface, and a device network interface (such as a wireless Wi-Fi interface). The system also comprises at least one test kit, such as a multiple-track lateral flow immunoassay test kit. This test kit will be generally configured to accept a sample, such as a liquid sample, from a sample collector, and analyze this sample for multiple analytes, such as multiple drugs of abuse. The test kit will be generally configured to report the results as a plurality of spatially separated optically detectable signals (e.g. immunoassay "lines") that report on the presence, absence, or relative levels of the various analytes.

In a preferred embodiment, to preserve privacy this test kit will be configured to display these spatially separated optically detectable signals (e.g. "lines") in a manner that is obfuscated according to an obfuscation code. That is, no test "key" (at least beyond control results) will be provided so that the operator can't just look at the test and see results that the sample donor may not have authorized. This "test answer key" provides the correspondence between the optically detectable signals and specific analytes, and is often called the test "obfuscation code". This obfuscation code can vary between different test kits, even of the same type, so as to make it more difficult for the operator, who does not have the correct obfuscation code, to interpret unauthorized test results.

The test kit is often configured with at least one test ID code, such as an optical test ID code (e.g. bar code or QR code), RFID code, NFC code, and the like that allows the computerized device to uniquely identify this specific test kit.

The system will often typically comprise a test reader stand configured to hold both the computerized device and the test kit so that the computerized device controlled' camera can image the test kit, and also obtain the test ID code (when the test kit is present). For example, if the test ID code is an optical bar code or optical QR test ID code, then the camera can also image the test optical ID code.

The computerized device software is typically configured to accept various operator entered analysis parameters for at least a subset of the plurality of analytes. That is, if the test ID code lets the system know that the test kit is for 18 different analytes, a menu selection of these 18 analytes can be presented, and the operator can pick among those of the 18 analytes that the operator is allowed to select according to various regulations and sample donor permissions.

The computerized device software is typically further configured to accept test reporting information (i.e. the electronic or physical address of a recipient (contact) who gets a copy of the test results), test details, and various types of information about the sample donor (sample donor information).

The computerized device software further configured so that, after the sample has been applied to the test kit, the test kit runs, and then the test kit is applied to the test kit reader stand, the camera can then image the test kit, obtain images of the spatially separated optically detectable signals (e.g. immunoassay "lines), and if one or more test optical ID codes are used, also obtain images of these test optical ID code(s).

Although in some embodiments, the computerized device may be configured to run in a stand-alone mode without using an external server (e.g. the computerized device may have its own version of the server database (202) to be discussed, and may itself implement the algorithms discussed in FIG. 9), in a preferred embodiment, the device will work with an external server, such as the server (200) shown in FIG. 1.

In a preferred embodiment, the device software will be further configured to use the device's network interface (such as a Wi-Fi wireless interface, wireless router, and internet connectivity) to transmit various data such as operator entered analysis parameters for at least a subset of the plurality of analytes (e.g. what analytes the operator selected), the reporting information, the test details, at least some sample donor information, the test ID code (possibly obtained from images of test optical ID codes), and images of the spatially separated optically detectable signals (e.g. the various immunoassay test kit "lines") to a remote server. In this preferred embodiment, to enhance privacy and security, the obfuscation code is stored on this remote server, and is not transmitted to either the handheld computerized device or the operator.

BRIEF DESCRIPTION OF THE DRAWINGS

FIG. 10B shows the bottom half of an example drug screen report that the system could send to a recipient.

DETAILED DESCRIPTION OF THE INVENTION

Figure 1:
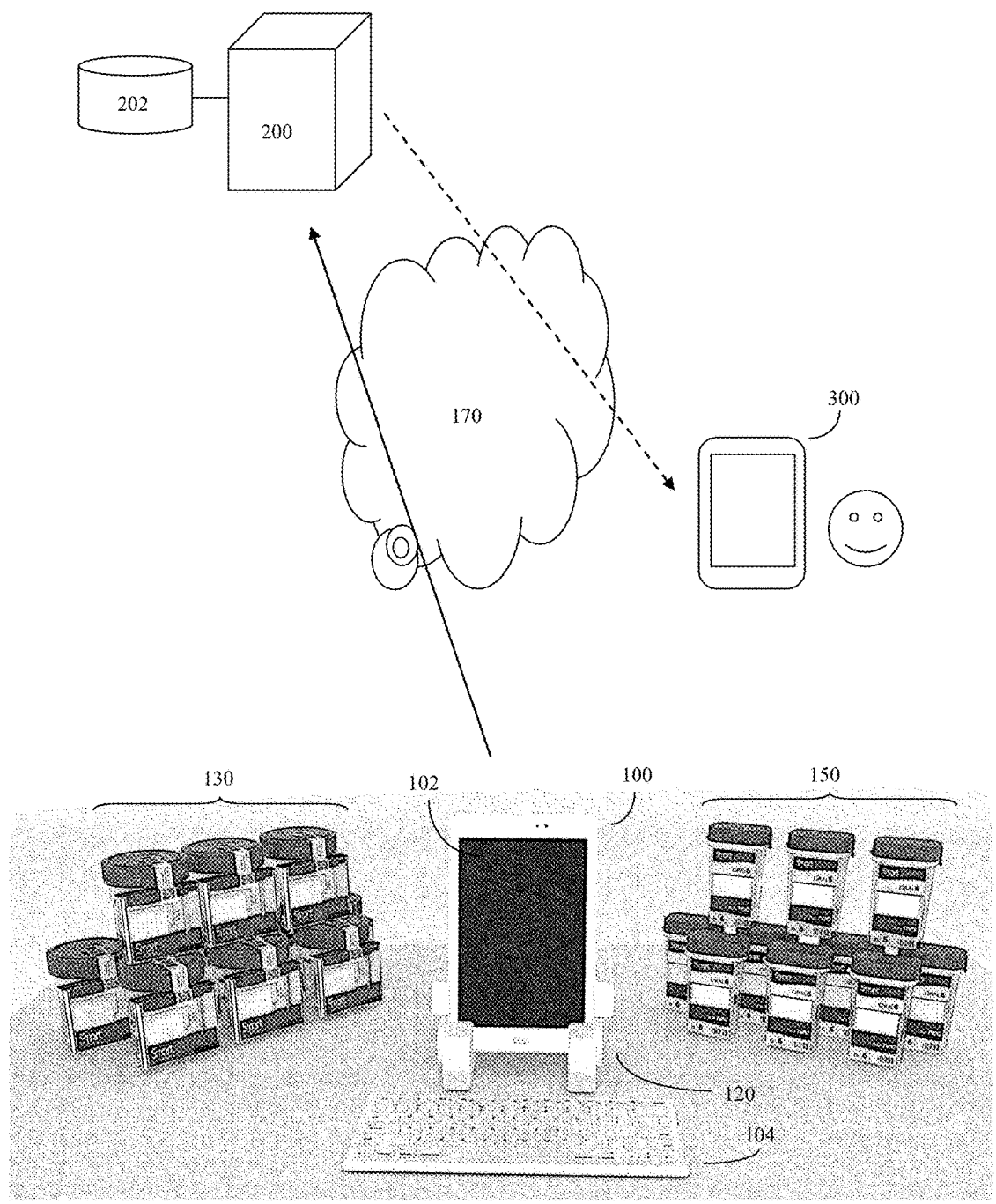
FIG. 1 shows an overview of the sample analysis system, here interacting with a remote server.

FIG. 1 shows an overview of the sample analysis system, showing the computerized device (here a handheld tablet computer 100) equipped with a camera, processor and software (not shown), with a user interface (here a touchscreen 102 and optional keyboard 104) and a wireless (Wi-Fi) connection to a computer network (here the internet 170). Various disposable test kits (each comprising a plurality of lateral flow immunoassays 130, 150) are also shown. A stand (120) configured to hold the tablet computer type computerized device and the test kit is also shown. The computerized device is configured to communicate (here over the Internet 170) to a remote server (200) and database (202). This remote server is in turn configured to transmit test result information to at least one recipient device (300).

Thus in FIG. 1, the system comprises a computerized device (handheld tablet device 100), comprising a processor, camera, device software, memory, touchscreen user interface, and a device network interface, such as a Wi-Fi wireless interface. An examples of a suitable handheld computerized device includes the Samsung Galaxy Tab series handheld tablet computer, which typically has a 1 GHz+ multiple core processor, 8+ gigabytes memory, 2+ megapixel camera, Wi-Fi wireless transceiver, touchscreen user interface, and which typically Android series operating system software.

Figure 4:
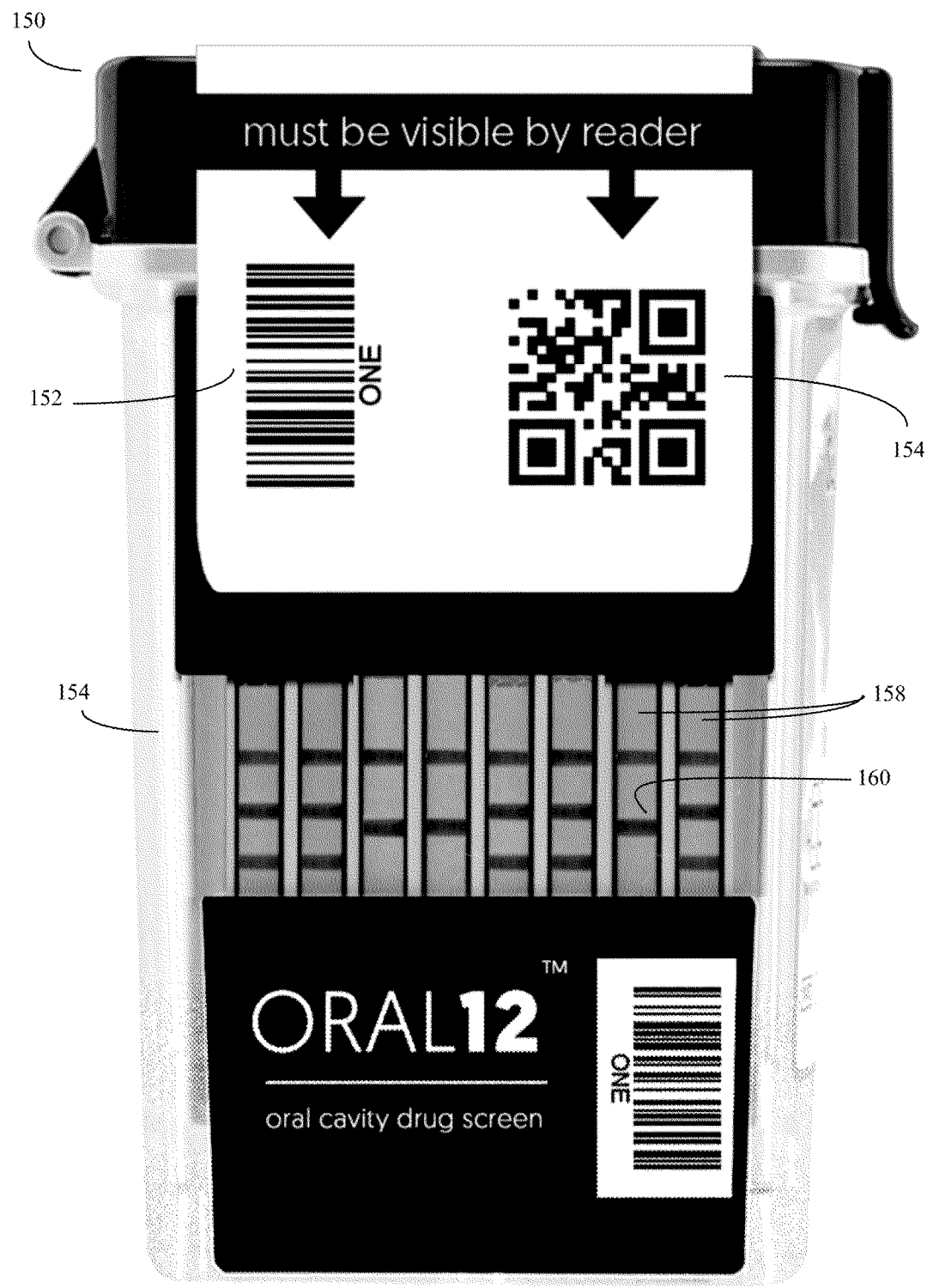
FIG. 4 shows a detail of one type of test kit.
Figure 5:
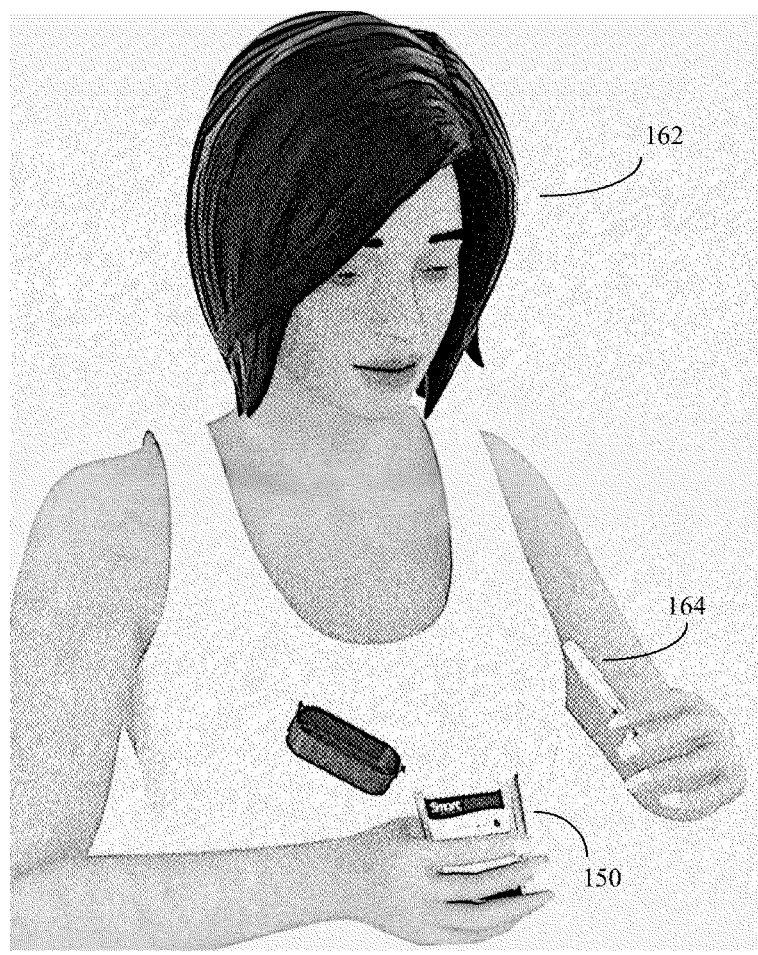
FIG. 5 shows an example of a sample donor using a sample collector to obtain an oral liquid sample.

As previously discussed, the system also comprises at least one disposable test kit (see 130, 150) configured to accept a liquid sample from a sample collector (see FIG. 5, (164), and analyze this liquid sample for a plurality of analytes, and display a plurality of spatially separated optically detectable signals (see FIG. 4 (160) reporting on this plurality of analytes. These test kits are typically configured for one-time use only, and cannot be reused.

The test kit also further comprises a test ID code (e.g. the test optical ID codes shown in FIGS. 4 (152), and (154) that uniquely identifies that particular test kit. That is, the test ID code not only identifies what type of test kit is being used, but also the specific identification number of this individual test kit. This helps to ensure that a previously run test kit is not accidentally reused.

Figure 3A:
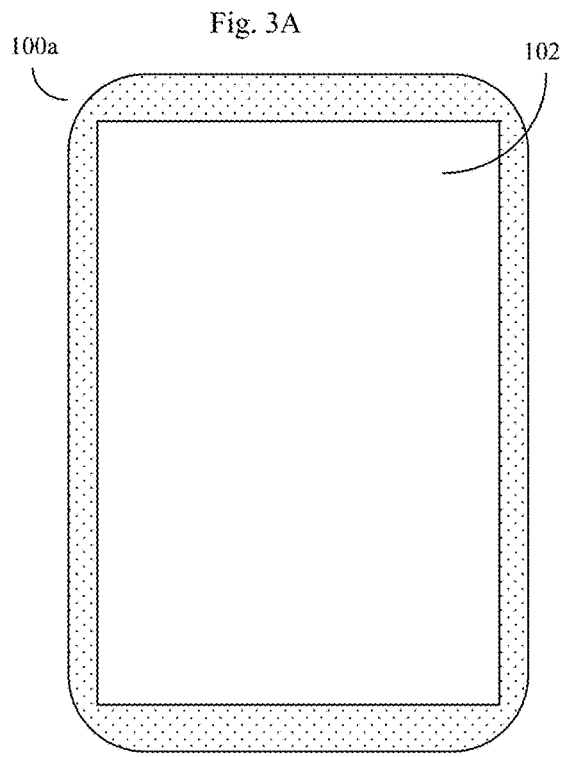
FIG. 3A shows a simplified image of the front of a handheld tablet type computerized device.
Figure 3B:
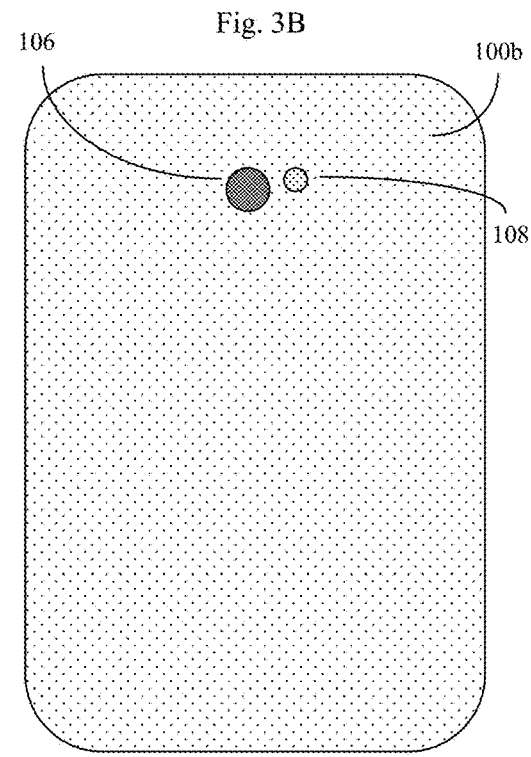
FIG. 3B shows a simplified image of the back of a handheld tablet type computerized device.
Figure 3C:
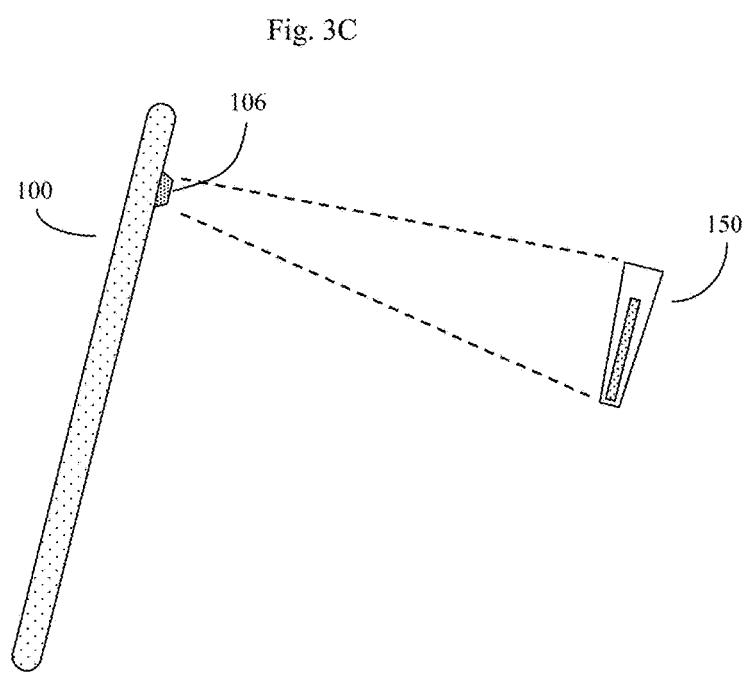
FIG. 3C shows a side view of the handheld tablet type computerized device, here positioned by a test reader stand so as to be able to use its video camera to image the test kit.

As previously discussed, the test reader stand (120) is configured to hold both the computerized device (such as the handheld tablet computer 100) and the test kit (e.g. 150) so that the device camera (see FIG. 3C, (106) can image the test kit (150) when the test kit is present on the test reader stand.

Figure 6:
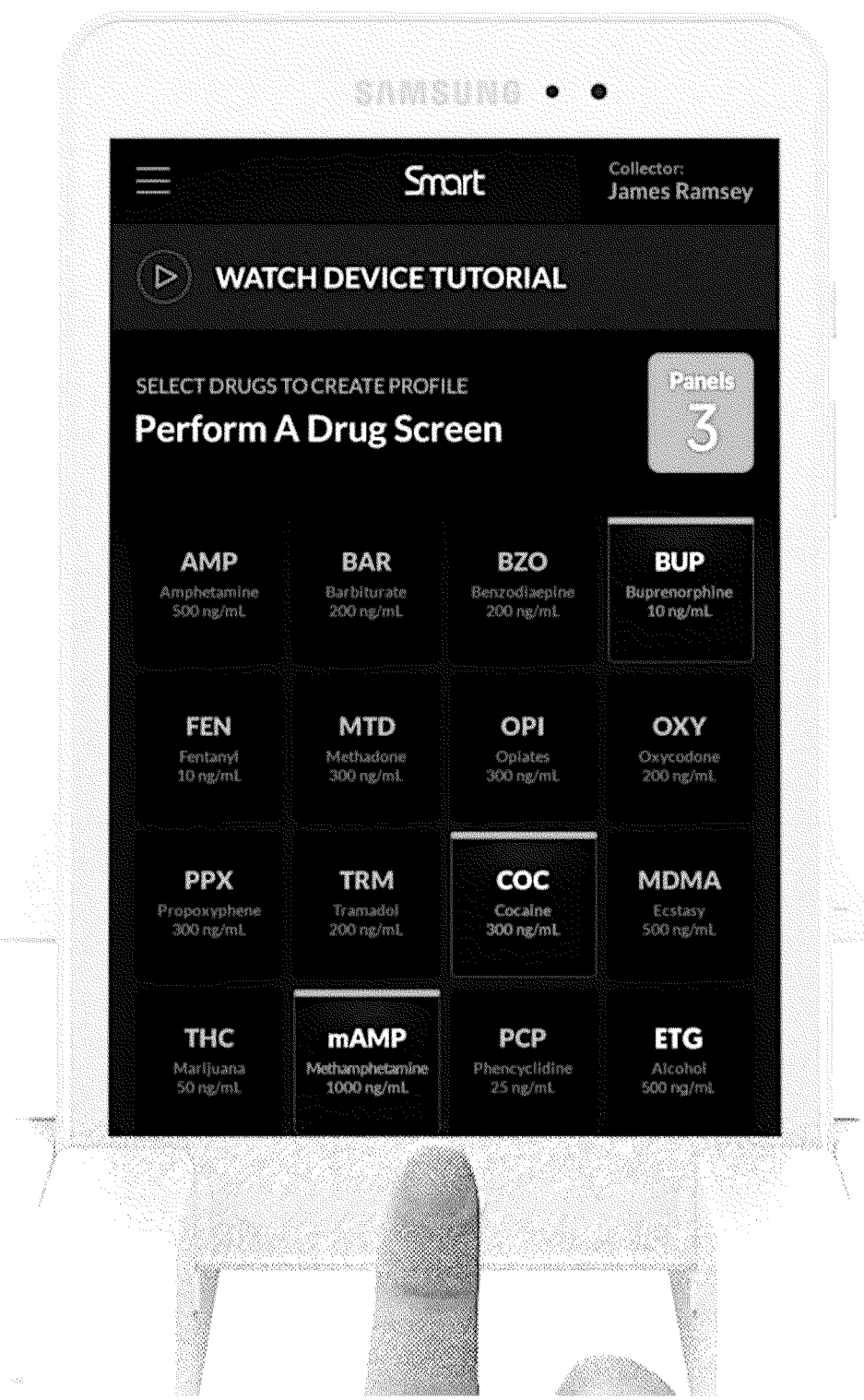
FIG. 6 shows an example of how the computerized device software can be configured to present a menu comprising various test analytes and sensitivity levels that the operator can choose to screen for, or not.
Figure 7:
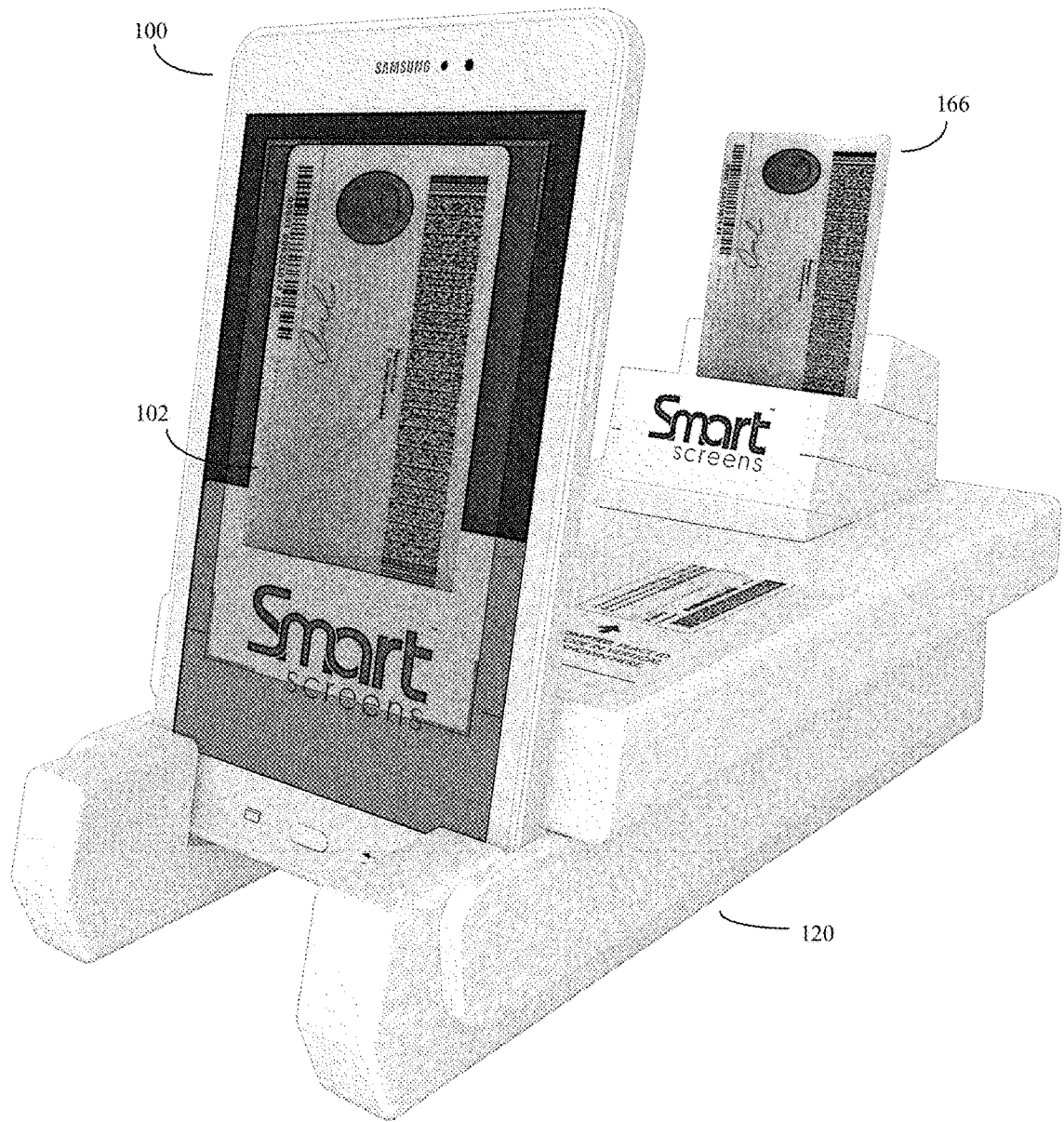
FIG. 7 shows an example of how the computerized device can obtain further information pertaining to the sample donor by using the device's camera to scan a donor identification card, such as a driver's license.
Figure 8:
FIG. 8 shows an example of how the computerized device can use its touchscreen, or other user interface such as a keyboard, to obtain additional information pertaining to the sample donor, obtain signatures, and designate a recipient for the test results.

As will be discussed shortly in more detail, and as shown in FIG. 6, the computerized device (100) software is typically configured to accept operator entered analysis parameters for a subset of the plurality of analytes that can be run by any given test kit. Thus, for example, even though a test kit might be configured to run 16 samples, the operator may only be authorized to run three of these samples. Also, as will be discussed shortly in more detail, and as shown in FIG. 7 and FIG. 8, the computerized device software is typically further configured to accept various types of test reporting information, test details, and at least some sample donor information. For example, as shown in FIG. 8, the test reporting information can comprise an electronic or physical address of at least one recipient (contact, here in FIG. 8 called Jane Doe") for the test reporting information. This allow test results to be relayed to the recipient's device (FIG. 1 300) using an optional server (200) over the internet (170), or by other method.

As previously discussed, the computerized device (100) is further configured to use the camera (106) to image the test kit (150) and obtain images of the spatially separated optically detectable signals, such as those shown in FIG. 4 (160).

In a preferred embodiment, the computerized device (100) software is further configured to use the device's network interface to transmit the various data, such as the operator entered analysis parameters for at least a subset of the plurality of analytes (e.g. what analytes and sensitivity ranges were chosen), the test reporting information, the test details, at least some data pertaining to the sample donor (e.g. sample donor information) to a remote server (FIG. 1, 200). The computerized device (100) will also usually transmit the test ID code (e.g. optical ID codes 152 154, or other ID codes), and images of the spatially separated optically detectable signals (160) to this remote server (200).

Often, the computerized device may use a Wi-Fi type interface, internet connected Wi-Fi router, and an internet connection to connect to an internet type computer network. However other wired and wireless network interfaces and other type networks may also be used.

Figure 2:
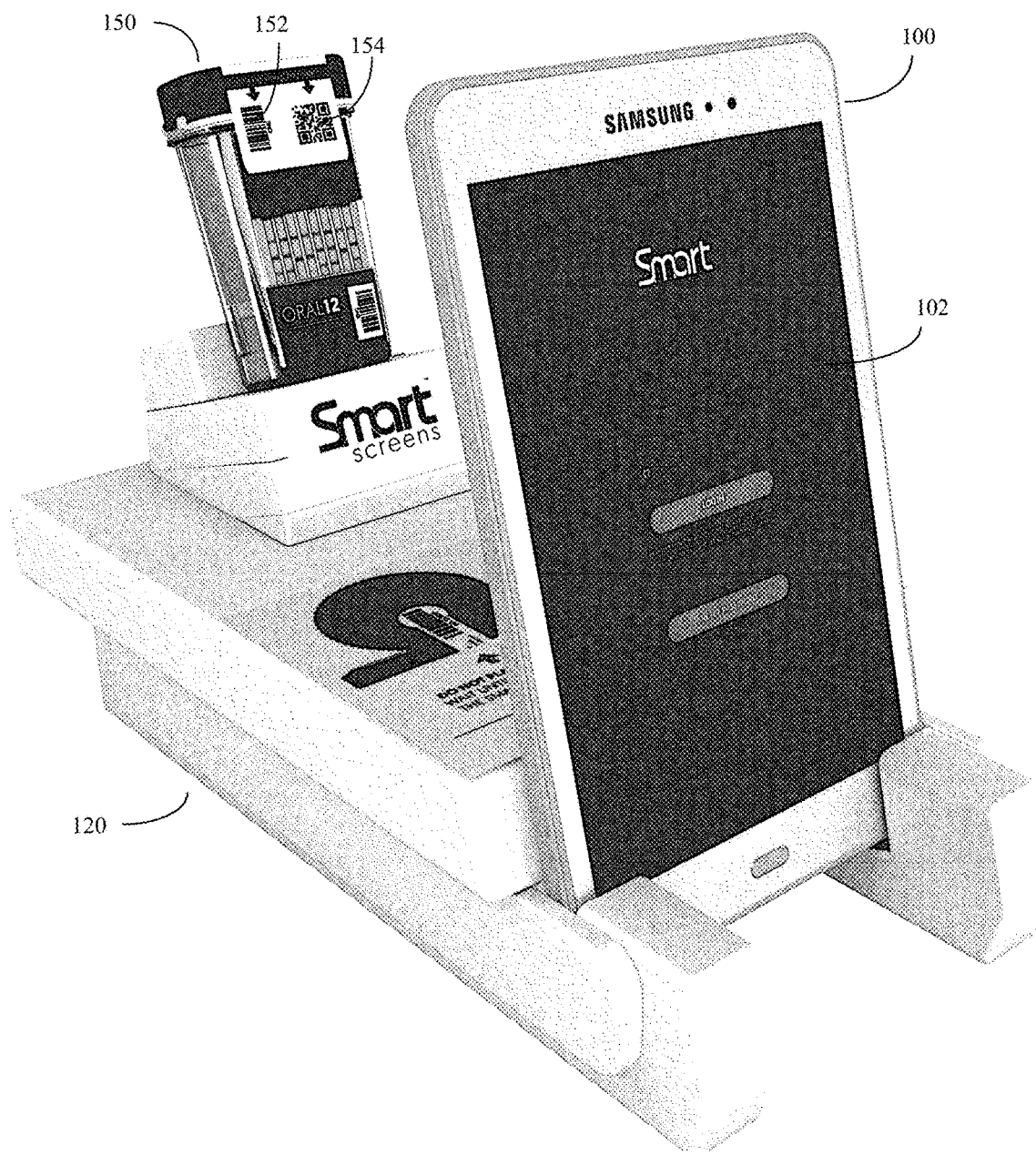
FIG. 2 shows some additional details of the computerized device, test reader stand, and test kit.

FIG. 2 shows some additional details of the computerized device (100), test reader (120) configured to hold the computerized device (110), and a test kit (150) configured with at least one test ID code (here one or more optical codes such as a bar code 152 and a QR code 154). Here a camera mounted on the back of the computerized device 100 (see FIG. 3B) is oriented to image the test kit 150, using either an ambient light source or a light source built into the computerized device or test reader (see FIG. 3B 108).

FIG. 3A shows a simplified image of the front (100*a*) of a handheld tablet type computerized device (100), such as the previously discussed Samsung Galaxy Tab handheld computerized device, here showing the front touchscreen of the device that can be oriented to allow a user to view the touchscreen.

FIG. 3B shows a simplified image of the back (100*b*) of a handheld tablet type computerized device, here showing a camera (106) that may be used to image the test kit, and an optional built-in light source (108) that can be used to supplement ambient light if desired.

Although for many such tests, standard office room lighting will provide enough ambient light in order to allow the camera (106) to image the test kit (150). However if the ambient light is inadequate, it may be supplemented by additional light sources, which may be built into the test reader stand (120), the computerized device (e.g. 108) or elsewhere as desired.

FIG. 3C shows a side view of the handheld tablet type computerized device (100), here positioned by the stand (not shown) so as to be able to use is camera (106) to image the test kit (150).

FIG. 4 shows a detail of one type of test kit (150). This test kit contains several optical test ID codes. Here two optical bar test ID codes (152) and one optical QR (154) test ID codes are shown. This test kit further comprises a transparent chamber (156) (or chamber with a transparent window) containing a plurality of lateral flow immunoassay tracks (158), here configured to generate multiple spatially separated optically detectable signals (160) (here the immunoassay lines) reporting on various analytes in an applied sample. In this example, assume that the analytes have already been analyzed. Note that in this example, there is no answer key on the surface of the immunoassay kit that indicates which lines correspond to the presence or absence of which analytes. Instead, these results are obfuscated according to an obfuscation code that, in some embodiments, is not known by the operator or the local computerized device (100), but that is known by the remote server and database (200, 202).

Put alternatively, in some embodiments, the test kit (130, 150) comprises a lateral flow immunoassay comprising a plurality of lateral flow immunoassay tracks (158) configured to generate at least one spatially separated optically detectable signal (160) reporting on at least one of the various analytes. In the example shown in FIG. 4, the test kit that is configured to report on 12 analytes has eight lateral flow immunoassay tracks, and 21 or more "lines" or regions where spatially separated optically detectable signals (160) are generated. Some of these "lines" or spatially separated optically detectable signals (160) are used for positive and negative controls (e.g. to inform if the test has been run properly, and others are used to detect for the actual analytes themselves).

Note that even in the FIG. 4 example, no "answer key" that allows the viewer to determine which spatially separated optical signal (160), e.g. which "line", corresponds to which drug. Often such answer keys are provided in the ancillary packaging and labeling associated with a test kit, so that the operator can visually match up the presence or absence of a particular "line" (or lack of a line) on a particular location of a particular track with a specific analyte.

In some embodiments, however, no such answer key, beyond perhaps a labeling that shows which "lines" and which tracks are control lines, will be provided to either the operator or the computerized device (100). Instead, this information is hidden or "obfuscated". Here the answer key that enables a human or machine to match up a given spatially separated optically detectable signal (e.g. the presence or absence of a line) will be termed an obfuscation code.

In some embodiments, the test kit manufacturer may take deliberate steps to make it harder for operators to guess which "lines" correspond to particular drugs or other analytes. For example, the pattern of lines may be changed from test to test. Here, however, the manufacturer will at least keep track of which test has which obfuscation code by assigning to each test kit a unique test ID code, and then keeping track of the association between an obfuscation code for a specific test kit, and that test kit's unique test ID, in a database such as database (202). Other obfuscation steps can include varying the position of control "lines", sometimes having two "lines" associated with the same analyte, and the like. The idea is to make it difficult for the test operator to casually glance at a test kit and determine, based on past experience, that the sample donor is positive for a specific analyte.

Thus, by using obfuscation code techniques, two sample donors who are both negative for all analytes, doing tests back to back with the same type of test kit, might produce a different pattern of lines (160). However, once the test ID codes are interpreted, and each analyzed with that specific test kits obfuscation code, the correct results, that both sample donors were negative for all analytes, will be obtained.

Although, in FIG. 4, the example test kit uses a test ID code comprising an optical bar code and an optical QR code, other types of test ID codes may be used. For example, in some embodiments, the test kit may use an RFID code chip, or an NFC code chip to report the test ID code. If the use of wireless type RFID code chips or NFC code chips is desired, in some embodiments, suitable RFID readers or NFC readers may optionally be built into the test reader stand (120) to facilitate reading these non-optical test ID codes. These RFID readers or NFC readers may, in turn, communicate the corresponding test ID codes to the computerized device (100).

FIG. 5 shows an example of a sample donor (162) using a sample collector (164) to obtain an oral liquid sample. Here the sample donor is also shown holding a test kit (150) and is shown about to deliver the liquid sample to the test kit. Alternatively, another individual, such as the system operator, may deliver the liquid sample to the test kit.

Various types of samples may be used by the system. Often the test sample may be a liquid sample, such as any of a urine, oral (e.g. saliva) blood body fluid sample, or alternatively a chemical liquid sample of an unknown chemical or other material that the operator wishes to analyze.

In some embodiments, the sample collector (164) itself may be placed on the test reader stand (120) and imaged by the computerized device (100). Here, the device or server software may be further configured to use the camera (106) to image the sample collector (164) after it has been filled with sample, and either analyze the adequacy of the liquid sample directly, and/or further transmit images of the sample collector to the remote server (200). This can be used to help document that a correct sample, and an adequate sample, has been analyzed.

More specifically, in some embodiments, at the server side, when upon receiving images of the sample collector (164) from the computerized device (100), the server software can be further configured to use these images of the sample collector to determine if the sample has adequate volume, adequate temperature, or evidence of improper handling. An image of the filled sample collector (164) may also be saved in the database (202) as part of the tests permanent record, and optionally transmitted to the recipient (300) as well.

FIG. 6 shows an example of how the computerized device software can be configured to present a menu comprising various test analytes and sensitivity levels that the operator can choose to screen for, or not. Here the operator has used the tablet computer's touchpad to select a subset of analytes (here the three analytes, BUP, COC, and mAMP), from the plurality of analytes (AMP—Amphetamine, BAR—Barbiturates, BZO—Benzodiazepines, BUP—Buprenorphine, FEN—Fentanyl, MTD—Methadone, OPI—Opiates, OXY—Oxycodone, PPX—Propoxyphene, TRM—Tramadol, COC—Cocaine, MDMA—Methylenedioxymethamphetamine (Ecstasy), THC—Marijuana, mAMP—Methamphetamine, PCP—Phencyclidine, ETG—Alcohol metabolite Ethyl Glucuronide) that could potentially be analyzed by the particular test kit being used.

ETG is another good example of an optional test that some organizations may prefer to skip. The alcohol metabolite ethyl glucuronide is found in many common products such as NyQuil, balsamic vinegar, mouthwash, and the like. For that matter, so long as an employee is not impaired on the job, in many occupations, what an employee does during off hours is their own business.

Note that in addition to selecting specific analytes, the system may additionally, or simultaneously with the selection, allow the operator to enter in additional operator entered analysis parameters such as operator entered sensitivity levels. Alternatively, these operator entered sensitivity levels may be assigned by default whenever the operator picks a specific analyte.

Although the system can in principle work with a test kit comprising only two analytes, where the system allows the operator to randomly pick either one or two of these analytes, this is more of a limiting example. As a general rule, the test kit will be capable of analyzing at least three analytes, and the system will allow the operator to select 1, 2, or all three of these analytes. There is no upper limit. Usually the test kit will be capable of analyzing at least three different analytes, and in general, for "n" analytes, the system will allow the user to select "n", or "n−1", or "n−2" . . . down to a minimum of 1 analyte, or even zero analytes if the operator merely wants to check that the system controls are operating properly.

Information pertaining to the (human) sample donor (162):

For drugs of abuse tests, and for that matter for any other medically or legally important test, it is often essential to establish a chain of custody for the test materials and results, and to verify that the data is accurate. One important way to do this is to include official information pertaining to the sample donor, such as images of government-issued cards and documents (here also called "cards"), and the like. Here we will use driver's licenses as an example.

FIG. 7 shows an example of how the computerized device (100) can obtain further information pertaining to the sample donor (162) by using the device's camera (106) to scan a donor identification card (166), such as a driver's license, or another type of "card".

In use, the sample donor might (162) be requested to both provide a copy of a government issued card or document, as well as to provide a signature consenting to the test.

Thus, in some embodiments, the device (100) software is further configured to obtain at least some of the sample donor information by using its camera (106) to also image a donor identification card (166) provided by the sample donor (162). This information can also be uploaded to the server (200) and database (202) as well.

Often just a driver's license image alone will not be enough, however. Additional information pertaining to the sample donor may also have to be provided.

FIG. 8 shows an example of how the computerized device (100) can use its touchscreen (102) or other user interface (e.g. keyboard 104) to obtain additional information pertaining to the sample donor (162), such as the sample donor's name, telephone number, signature, and signed consent to perform testing. The computerized device can also be used to inform the user, or the system, or both about the electronic or physical address of at least one recipient (300) for the test reporting information.

Thus, given that the computerized device (100) will typically be configured to transmit at least some of this sample donor information to the remote server (200), it becomes the responsibility of the server processor and software (200) to keep track of this sample donor information, and to merge it with the test results and other data.

More specifically, in cases where the computerized device (100) is further configured to obtain at least some of the sample donor information by using its camera (106) to image a donor identification card (166) provided by the sample donor, and to further transmit images of this donor identification card to the remote server (200), the server software can be further configured to use these images of the donor identification card to determine at least some this sample donor information. For example, in the case of a driver's license, in addition to storing an image of the donor identification card, the server may use image recognition software or optical character recognition card to extract information, such as the driver's license number, from the card.

Note that there are other types of identification, such as passports and birth certificates that although are not "cards" can still contain the same type of useful identification information. Here the term "card" is intended to refer to any document useful for identity verification purposes.

For quality control purposes, it will often be useful to configure the computerized device (100) software to display captured images on its display screen (102) before making use of the images, so that the operator can catch obvious problems, such as poor card or test kit positioning on the test kit stand (120), poor ambient light, and the like. Thus, for example, in FIG. 7, the computerized device is showing an image of the donor identification card (166) on its display screen (102) for operator verification before then processing this image. In a similar manner, in some embodiments, the device (100) software is often configured to use the computerized device to display images of the test kit's spatially separated optically detectable signals (160) to the operator prior to transmission, and to obtain operator input authorizing transmission, before transmitting images of these spatially separated optically detectable signals (these images will look a lot like FIG. 4) to the remote server (200).

Figure 9:
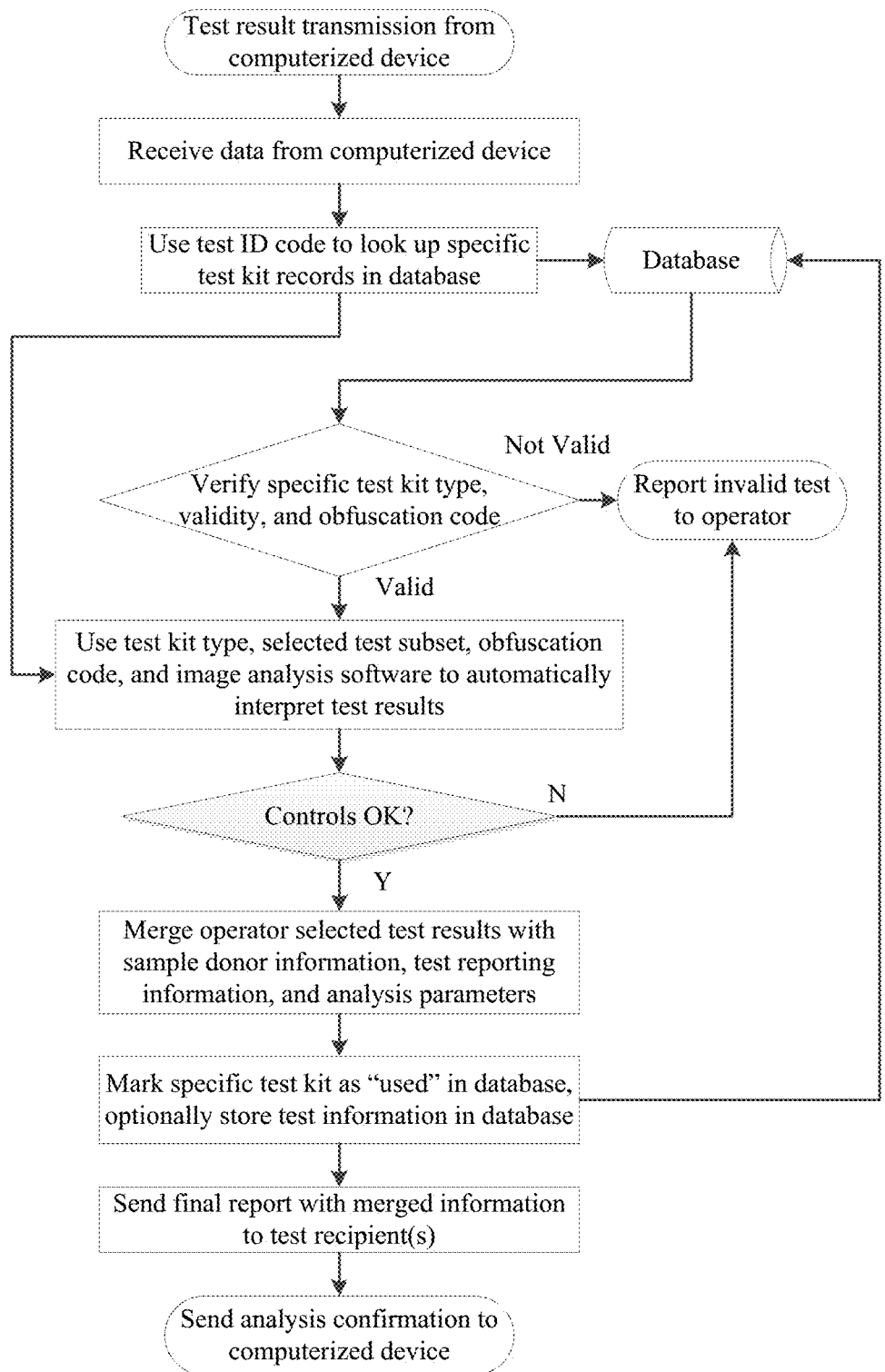
FIG. 9 shows a flowchart providing additional details of how the system's remote server can use records of the association between specific test ID codes and specific test kits to interpret images of the spatially separated optically detectable signals.

FIG. 9 shows a flowchart providing additional details of how the system's remote server (200) can use records of the association between specific test ID codes (152, 154) and specific test kits (150) to interpret images of the spatially separated optically detectable signals (160). In some embodiments, as previously discussed, these spatially separated optically detectable signals may be obfuscated by an obfuscation code. In these embodiments, usually the server database (202) will store an association between a specific test ID code (154), and the obfuscation code needed to interpret the results (160). The server (200) can also use the various operator entered analysis parameters (see FIG. 6), test reporting information (see FIG. 8), and at least some sample donor information (see FIG. 7) to transmit information about these analytes to at least one recipient (300).

More specifically, in some embodiments, the remote server (200) comprises at least one processor, memory, database, server software, and server network interface to a computer network such as the internet (170). The database (202) will typically comprise records associating specific test ID codes (152 or 154) with a list of a plurality of test analytes analyzed by a specific test kit that has that specific test ID code (152, 154). The database will also store records regarding the properties of this specific test kit. These properties can include which tests that test kit is configured to analyze, expiration date of the test kit, if the test kit has been run before or not (in which case an error should be reported) and an obfuscation code (answer key) that tells the server which "lines" correspond to which specific test analytes, which lines correspond to which controls, what control results are associated with a properly run test, and what control results are associated with an improperly run test.

The server software will typically be configured to use the server's network interface to receive, from the computerized device (100), the previously discussed operator entered analysis parameters for at least a subset of the plurality of analytes (see FIG. 6), the test reporting information and test details (see FIG. 8), at least some of the sample donor information (see FIG. 7 and/or FIG. 8), the test ID code (e.g. FIG. 4 154), and images (see FIG. 3C 106, 150) of the spatially separated optically detectable signals (160).

To determine these spatially separated optically detectable signals (160), the server software will often be further configured use image interpretation software to determine these spatially separated optically detectable signals from the images of the spatially separated optically detectable signals uploaded by the computerized device (100). Alternatively, this image interpretation software can be implemented by the computerized device (100) software, in which case only the data from the spatially separated optically detectable signals (e.g. presence or absence of a positive, or optical intensity data) needs to be uploaded to the server. Similarly, any test optical ID codes can also be imaged by the computerized device, interpreted by the local device's software, and only the actual test ID code results (e.g. the data encoded by the test ID code) uploaded to the server.

The server software will often be further configured to use the operator entered analysis parameters (e.g. which tests to analyze, and sensitivity levels requested by the operator, see FIG. 6), and the test reporting information (see FIG. 8), and at least some of the sample donor information (see FIG. 7 and/or FIG. 8) to transmit information pertaining to a status of those analytes chosen by the operator to at least one recipient or contact (300) specified by the test reporting information (see FIG. 8).

Note, however, that the server software will also be evaluating the status of any test controls using control "lines" (160) and that test kits obfuscation code (if any). If the controls are invalid, then instead usually an error message will be sent back to the computerized device (100) and the test operator, and no test results will be sent to the recipient.

Further, as previously discussed, in a preferred embodiment, where the test kit is configured to display the spatially separated optically detectable signals (160) in a manner that is obfuscated according to an obfuscation code. This obfuscation code will typically be stored on the remote server (200) and is not transmitted to either the computerized device (100) or the computerized device operator.

Here, instead, the database (202) will typically comprise records associating specific test ID codes (154) with a list of a plurality of test analytes analyzed by that specific test kit that has that specific test ID code, as well as information pertaining to the properties of that specific test kit (expiration date, sensitivity ranges), and that specific test kit's obfuscation code (answer key).

The server software is typically further configured to use the database (202) and the test ID code (154) to retrieve that specific test kit's obfuscation code from the database, and to use this specific test kit obfuscation code (answer key) and the spatially separated optically detectable signals (e.g. lines 160) to determine a presence of any analytes in the plurality of analytes analyzed by that specific test kit.

In some embodiments, when the test ID code is a test optical ID code (such as 152 or 154), and wherein the camera (106) uses ambient light to image the test kit and the test optical ID code, the test code can help provide important black and white and color balance information to assist in interpreting the test kit images. Here the computerized device (100) can further use its camera (106) to transmit an image of the test ID code (152, 154) to the server (200). The server software can further use the white or black or color balance information from the test optical ID code or codes to correct the images of the spatially separated optically detectable signals (160) for differences in ambient light. Other color references may also be provided on the test kit to aid in image correction as well.

Thus if, for example, the ambient light is too dim, or has an incorrect color balance that might tend to diminish the reliability of the camera images of the test results, the server can either correct for this using the known optical properties of the test optical ID code (e.g. white on black over a uniform area) or other color reference to either correct the images, or else report an error if the ambient light is not adequate.

It should be noted that with time, server (200) and database (202) will accumulate a vast amount of data regarding the results of hundreds of thousands or even millions of different tests. With such large amounts of data, various types of statistical analysis or even machine learning techniques may be employed in order to further improve the reliability of the system.

Thus, in some embodiments, where the database (202) further comprises test results from a plurality of different previously run test kits, the server software can further be configured with historical statistical analysis obtained from statistically analyzed results from at least some of the various previously run test kits. Here the server software can be further configured to use this historical statistical analysis to help better determine the presence or absence of various test analytes. For example, if historical data shows that a particular analyte is tending to generate false positives, the server might compensate by somewhat altering the image thresholds used to determine if a test is positive or negative.

Figure 10A:
FIG. 10A shows the top half of an example drug screen report that the system could send to a recipient.

FIG. 10A shows the top half of an example drug screen report that the system could send to a recipient. Here data from different sources are merged to provide an easy to read overall report. This top half contains donor information such as the name, birthday, driver's license number, which might have been reported from an OCR reading of the driver's license (166) as shown in FIG. 7. The top half also contains information about the operator (collector) of the local computerized device (100), and information about the recipient (e.g. the organization that ordered the test), which might have been obtained by direct input into the computerized device (100) as shown in FIG. 8. The test data is also provided, along with various test results ordered by the operator.

Note that here, the computerized device (100) was further configured to collect additional test details. These test details can be additional test information such as the test location, test type, date of test, operator (collector's) name, address, phone number, email, password, and the like. The server software was further configured to transmit at least some of these test details to the at least one recipient (300). In FIG. 10A, these test details included the collector (operator's) first and last name, phone number, email address, company, and physical address, but the password was not reported by the server.

FIG. 10B shows the bottom half of an example drug screen report that the system could send to a recipient (300). In this bottom half, additional information, such as the donor's signature authorizing the test is provided, which was previously shown being entered in FIG. 8. Information about the test device including the lot number and expiration date, which the system computed by using the test ID code (152 or 154) and the server database (202) are also provided. Additional information pertaining to the validity of the test sample, which may have been obtained by either optical scanning of the test kit itself (150) and/or the sample collector (164), is also provided, along with some additional test results. Note that because the sample donor was negative for all requested tests, the system is also reporting an overall "negative" result for convenience.

Thus, in some specific embodiments where the system uses a remote server (200) and database, this database (202) can comprise records associating specific test optical ID codes (152, 154) with a list of a plurality of test analytes analyzed by a specific test kit (150) with that specific test kit's optical ID code, and the properties of that specific test kit, and that specific test kit's obfuscation code (answer key). The server software is often configured to use that server's network interface to receive (over the internet 170), from the handheld computerized device (100), the operator entered analysis parameters for at least a subset of the plurality of analytes (e.g. tests and sensitivity levels chosen), the test reporting information, any additional test details, at least some sample donor information, images (or results from) of the test optical ID code(s) (152, 154), and images of the spatially separated optically detectable signals (160).

If not already extracted by the computerized device (100), the server software is often further configured use image interpretation software to determine the test optical ID code from the images of the test optical ID code, and/or to determine the spatially separated optically detectable signals (e.g. data as to if there is a positive signal or not, and if so how intense) from the images of these spatially separated optically detectable signals.

The server software further is often configured to use the database (202) and the test optical ID code to retrieve that specific test kit's obfuscation code (answer key) from the database (202), and to use that specific test kit's obfuscation code, and the optical scans of the spatially separated optically detectable signals, to determine a presence of either all analytes or operator selected analytes in the various analytes run by that specific test. For quality assurance purposes, the system can also check to be sure that the specific test kit was not used before, had not expired, and that the controls were running OK.

The server software will also typically be configured to use the operator entered analysis parameters (FIG. 6), the test reporting information (FIG. 8), and at least some sample donor information (such as FIG. 7 and/or FIG. 8) to transmit information pertaining to a status of those analytes chosen by the operator to at least one recipient (300) specified by the test reporting information (FIG. 8). As previously discussed, an example of such transmitted information is shown in FIG. 10A and FIG. 10B.

An earlier version of this invention was described in the inventor's video presentation, ""*Smart Screens™, the next generation drug testing system*", Vimeo video, uploaded to https://vimeo.com/232157802 by inventors James Taylor Ramsey and Stephen David Gobin DBA "Smart Screens" on Sep. 2, 2017. An alternate version of this invention was described in the inventor's video presentation, ""*Welcome to Smart Screens on Vimeo*", Vimeo video, uploaded to https://vimeo.com/255424927 by inventors James Taylor Ramsey and Stephen David Gobin DBA "Smart Screens" on Feb. 12, 2018. Another version of this invention was described in the inventor's video presentation, "*How Smart Screens works*", uploaded to https://vimeo.com/255425195 by inventors James Taylor Ramsey and Stephen David Gobin DBA "Smart Screens" also Feb. 12, 2018. Another version of this invention was described in the inventor's video presentation, "*Smart Screens—the future of drug testing*", uploaded to https://vimeo.com/277788869 by inventors James Taylor Ramsey and Stephen David Gobin DBA "Smart Screens" on Jun. 30, 2018.

The invention claimed is:

1. A sample analysis system, said system comprising:
   a computerized device comprising a processor, camera, device software, memory, user interface, and a device network interface;
   a test kit configured to accept a liquid sample from a sample collector, analyze said liquid sample for a plurality of analytes, and display a plurality of spatially separated optically detectable signals reporting on said plurality of analytes;
   wherein said test kit comprises a lateral flow immunoassay comprising a plurality of lateral flow immunoassay tracks configured to generate at least one spatially separated optically detectable signal reporting on at least one of said plurality of analytes;
   said test kit configured to display said spatially separated optically detectable signals in a manner that is obfuscated according to an obfuscation code;
   said test kit further comprising a test ID code uniquely identifying said test kit;
   a test reader stand configured to hold said computerized device and said test kit so that said camera can image said test kit when said test kit is present;
   said device software configured to accept operator entered analysis parameters for a subset of said plurality of analytes, said device software configured to further accept test reporting information, test details, and at least some sample donor information;
   said test reporting information comprising an electronic or physical address of at least one recipient (contact) for said test reporting information;
   said device software further configured to use said camera to image said test kit, and obtain images of said spatially separated optically detectable signals;
   said device software further configured to use said device network interface to transmit said operator entered analysis parameters for at least a subset of said plurality of analytes, said test reporting information, said test details, at least some said sample donor information, said test ID code, and images or data of said spatially separated optically detectable signals to a remote server; and
   wherein said obfuscation code is stored on said remote server and is not transmitted to either said computerized device or said operator.

2. The system of claim 1, wherein said device software is further configured to obtain at least some of said sample donor information by using said camera to image a donor identification card provided by said sample donor.

3. The system of claim 1, wherein said operator entered analysis parameters further comprise operator entered sensitivity levels.

4. The system of claim 1, wherein said liquid sample comprises any of a urine, oral, blood, or chemical liquid sample.

5. The system of claim 1, wherein said software is further configured to use said camera to image said sample collector after it has been filled with sample; and further transmit images of said sample collector to said remote server.

6. The system of claim 1, wherein said test ID code comprises any of an optical bar code, optical QR code, RFID code, or a NFC code.

7. The system of claim 1, wherein said device network interface is a Wi-Fi interface, and said network further comprises the internet.

8. The system of claim 1, wherein said analytes comprise analytes for drugs of abuse, and wherein said plurality of analytes comprises at least 3 analytes.

9. The system of claim 1, wherein said device software is configured to use said computerized device to display images of said spatially separated optically detectable signals to said operator prior to transmission, and to obtain operator input authorizing transmission, before transmitting said images of said spatially separated optically detectable signals to said remote server.

10. The system of claim 1, wherein said remote server comprises at least one processor, memory, database, server software, and server network interface to a computer network;
   said database comprising records associating specific test ID codes with a list of a plurality of test analytes analyzed by a specific test kit with said specific test ID code, and properties of said specific test kit;

said server software configured to use said server network interface to receive, from said computerized device, said operator entered analysis parameters for at least a subset of said plurality of analytes, said test reporting information, said test details, at least some said sample donor information, said test ID code, and images or data of said spatially separated optically detectable signals;

said server software further configured to determine said spatially separated optically detectable signals from images or data of said spatially separated optically detectable signals;

said server software further configured to use said operator entered analysis parameters, said test reporting information, and at least some said sample donor information to transmit information pertaining to a status of those analytes chosen by said operator to at least one recipient specified by said test reporting information.

11. The system of claim 10, wherein said sample is a liquid sample, and wherein said device software is further configured to use said camera to image said sample collector after it has been filled with sample, and to further transmit images of said sample collector to said remote server;

said server software further configured to use said images of said sample collector to determine if said sample has any of adequate volume, adequate temperature, or evidence of improper handling.

12. The system of claim 10, wherein said device software is further configured to obtain at least some of said sample donor information by using said camera to image a donor identification card provided by said sample donor, and to further transmit images of said donor identification card to said remote server;

said server software further configured to use said images of said donor identification card to determine at least some said sample donor information.

13. The system of claim 10, wherein said database further comprises test results from a plurality of different previously run test kits;

said server software further configured with historical statistical analysis obtained from statistically analyzed results from at least some of said plurality of different previously run test kits; and said server software further configured to use this historical statistical analysis to help determine a presence of any analytes in said plurality of analytes.

14. The system of claim 10, wherein said database further comprises records associating specific test ID codes with a list of a plurality of test analytes analyzed by a specific test kit with said specific test ID code, properties of said specific test kit, and said specific test kit's obfuscation code;

said server software further configured to use said database and said test ID code to retrieve said specific test kit obfuscation code from said database, and to use said specific test kit obfuscation code and said spatially separated optically detectable signals to determine a presence of any analytes in said plurality of analytes.

15. The system of claim 10, wherein said test ID code is a test optical ID code, and wherein said camera uses ambient light to image said test kit and said test optical ID code, and wherein computerized device further uses its camera to transmit an image of said test ID code to said server, and said server software further uses any of white or color balance information from said test optical ID code to correct said images of said spatially separated optically detectable signals for differences in ambient light.

16. The system of claim 10, wherein said computerized device is further configured to collect test details comprising any of test location, test type, and password;

and wherein said server software is further configured to transmit at least some of said test details to said at least one recipient.

17. A sample analysis system, said system comprising:

a handheld computerized device comprising a processor, camera, device software, memory, user interface, and a device network interface;

a test kit configured to accept a liquid sample from a sample collector, analyze said liquid sample for a plurality of analytes, and display a plurality of spatially separated optically detectable signals reporting on said plurality of analytes;

wherein said test kit comprises a lateral flow immunoassay comprising a plurality of lateral flow immunoassay tracks configured to generate at least one spatially separated optically detectable signal reporting on at least one of said plurality of analytes;

said test kit configured to display said spatially separated optically detectable signals in a manner that is obfuscated according to an obfuscation code;

said test kit further comprising a test optical ID code uniquely identifying said test kit;

a test reader stand configured to hold said handheld computerized device and said test kit so that said camera can image said test kit and said test optical ID code when said test kit is present;

said device software configured to accept operator entered analysis parameters for at least a subset of said plurality of analytes, said device software configured to further accept test reporting information, test details, and at least some sample donor information;

said test reporting information comprising an electronic or physical address of at least one recipient (contact) for said test reporting information;

said device software further configured to use said camera to image said test kit, and obtain images or data of said test optical ID code and images or data of said spatially separated optically detectable signals;

said device software further configured to use said device network interface to transmit said operator entered analysis parameters for at least a subset of said plurality of analytes, said test reporting information, said test details, at least some said sample donor information, images or data of said test optical ID code, and images or data of said spatially separated optically detectable signals to a remote server;

wherein said obfuscation code is stored on said remote server, and is not transmitted to either said handheld computerized device or said operator.

18. The system of claim 17, wherein said remote server comprises at least one processor, memory, database, server software, and server network interface to a computer network;

said database comprising records associating specific test optical ID codes with a list of a plurality of test analytes analyzed by a specific test kit with said specific test optical ID code, properties of said specific test kit, and said specific test kit's obfuscation code;

said server software configured to use said server network interface to receive, from said handheld computerized device, said operator entered analysis parameters for at least a subset of said plurality of analytes, said test reporting information, said test details, at least some said sample donor information, images or data of said test optical ID code, and images or data of said spatially separated optically detectable signals;

said server software further configured to determine said test optical ID code from said images or data of said test optical ID code, and to determine said spatially separated optically detectable signals from images or data of said spatially separated optically detectable signals;

said server software further configured to use said database and said test optical ID code to retrieve said specific test kit obfuscation code from said database, and to use said specific test kit obfuscation code and said spatially separated optically detectable signals to determine a presence of any analytes in said plurality of analytes;

said server software further configured to use said operator entered analysis parameters, said test reporting information, and at least some said sample donor information to transmit information pertaining to a status of those analytes chosen by said operator to at least one recipient specified by said test reporting information.

\* \* \* \* \*